United States Patent

Suzuki et al.

[11] 4,388,421
[45] Jun. 14, 1983

[54] N-(2-HYDROXY-3-METHACRYLOYLOXY-PROPYL)-AMINOBENZOIC ACID DERIVATIVES AND DENTAL ADHESIVE COMPOSITION CONTAINING SAME

[75] Inventors: Shin-ichi Suzuki, Odawara; Shinya Kitoh, Hiratsuka; Haruhiko Toda, Odawara; Moriaki Higo, Ninomiya, all of Japan

[73] Assignee: Lion Corporation, Tokyo, Japan

[21] Appl. No.: 330,605

[22] Filed: Dec. 14, 1981

[30] Foreign Application Priority Data

Dec. 20, 1980 [JP] Japan ............................ 55-181066
Dec. 20, 1980 [JP] Japan ............................ 55-181067

[51] Int. Cl.³ .................... C08K 5/10; C08K 5/16
[52] U.S. Cl. ..................... 523/118; 260/998.11; 433/217; 433/228; 560/221
[58] Field of Search ................ 523/109, 118; 260/998.11, 560/221; 433/217, 226, 228

[56] References Cited

U.S. PATENT DOCUMENTS 3,514,473  5/1970  McFadden et al. ............. 560/221
4,087,619  5/1978  Parks .............................. 560/221
4,119,610  10/1978  Kaelble ........................... 560/221

Primary Examiner—John Kight, III
Assistant Examiner—Amelia B. Yarbrough
Attorney, Agent, or Firm—Birch, Stewart, Kolasch & Birch

[57] ABSTRACT

Novel compounds used as polymerizable monomers in a dental adhesive composition, and having a general formula (1):

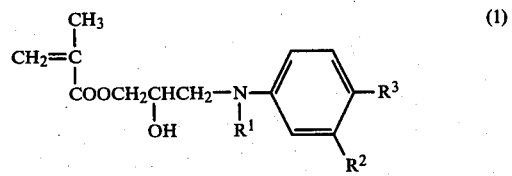

wherein $R^2$ is a carboxyl group and $R^3$ is a hydrogen atom when $R^1$ is a methyl group, and $R^2$ is a hydroxyl group and $R^3$ is a carboxyl group when $R^1$ is a hydrogen atom, that is, N-methyl-N-(2-hydroxy-3-methacryloyloxypropyl)-m-aminobenzoic acid and 2-hydroxy-4-[(2-hydroxy-3-methacryloyloxypropyl)amino]benzoic acid are disclosed.

10 Claims, 4 Drawing Figures

N-(2-HYDROXY-3-METHACRYLOYLOXY-PROPYL)-AMINOBENZOIC ACID DERIVATIVES AND DENTAL ADHESIVE COMPOSITION CONTAINING SAME

BACKGROUND OF THE INVENTION

This invention relates to novel compounds used as polymerizable monomers in a dental adhesive composition, and having a general formula (1):

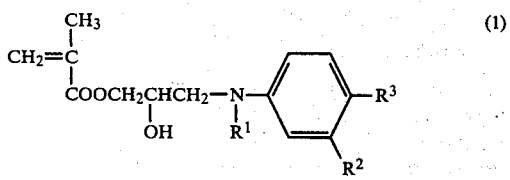

wherein $R^2$ is a carboxyl group and $R^3$ is a hydrogen atom when $R^1$ is a methyl group, and $R^2$ is a hydroxyl group and $R^3$ is a carboxyl group when $R^1$ is a hydrogen atom. They are N-methyl-N-(2-hydroxy-3-methacryloyloxypropyl)-m-aminobenzoic acid and 2-hydroxy-4-[(2-hydroxy-3-methacryloyloxypropyl)-amino]benzoic acid.

For the treatment of dental caries, composite resins were developed as a substitute for conventional dental cements such as zinc phosphate cement and silicate cement. Recently, improved composite resins are available which are stable for a prolonged period of time, because of reduced water-absorption and degradation, and exhibit very little difference in color from natural teeth.

However, since composite resins do not essentially adhere to tooth enamel or dentin, there is the likelihood that a gap is formed between tooth cavity and composite resin embedded therein over a long period of time. Such a gap tends to facilitate secondary caries and eventually a filled composite resin will fall from the cavity.

To improve the adhesion between composite resin and cavity wall, a variety of adhesion promotors or adhesive liners have been developed. Also proposed are adhesive caries-preventive filling materials, malaligned tooth orthodontic adhesives, and other dental adhesive compositions which solely aim at firm adhesion to tooth substances. Most of them have problems with respect to durability in the mouth and easiness of handling and few materials can firmly adhere to tooth for a long period of time in a wet, temperature-varying environment like the mouth.

SUMMARY OF THE INVENTION

Making extensive investigations for compounds which have increased adhesion to a tooth and which are advantageously used as polymerizable monomers in a dental adhesive composition, the inventors have discovered novel compounds having a general formula (1):

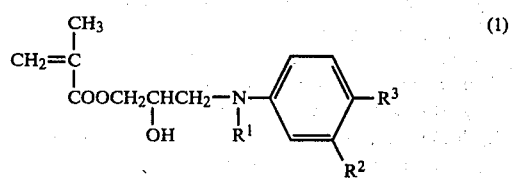

wherein $R^2$ is a carboxyl group and $R^3$ is a hydrogen atom when $R^1$ is a methyl group, and $R^2$ is a hydroxyl group and $R^3$ is a carboxyl group when $R^1$ is a hydrogen atom. They are N-methyl-N-(2-hydroxy-3-methacryloyloxypropyl)-m-aminobenzoic acid and 2-hydroxy-4-[(2-hydroxy-3-methacryloyloxypropyl-)amino]benzoic acid. According to the inventors' findings, cured products obtained by polymerizing or curing these compounds show increased adhesion to a tooth even in water, and polymers of these compounds of formula (1) or copolymers of the compounds of formula (1) with other monomers, when used as a dental filling material, firmly adhere to a tooth cavity wall so that neither formation of a gap nor falling of the filling material due to poor adhesion will occur, and when used as a primer or adhesive for a filling material such as a composite resin, provide improved material sealing so that secondary caries is effectively prevented. All these features prove that the compounds of formula (1) may be advantageously used as polymerizable monomers in a dental adhesive composition.

It is, therefore, an object of the present invention to provide novel compounds of formula (1) which are used as polymerizable monomers in a dental adhesive composition.

It is another object of the present invention to provide a dental adhesive composition which comprises one or both of the novel compounds of formula (1) and is used for the purpose of adhesion to tooth.

These and other objects, features and advantages of the present invention will become apparent from the following description.

DETAILED DESCRIPTION OF THE INVENTION

The novel N-(2-hydroxy-3-methacryloyloxypropyl)-aminobenzoic acid derivatives according to the present invention are represented by formula (1), and include N-methyl-N-(2-hydroxy-3-methacryloyloxypropyl)-m-aminobenzoic acid having the formula (2):

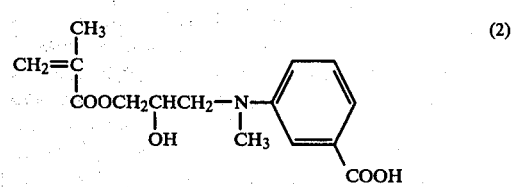

and 2-hydroxy-4-[(2-hydroxy-3-methacryloyloxypropyl)-amino]benzoic acid having the formula (3):

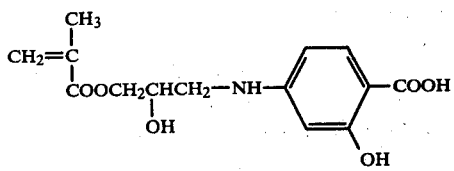

(3)

Figure 1:
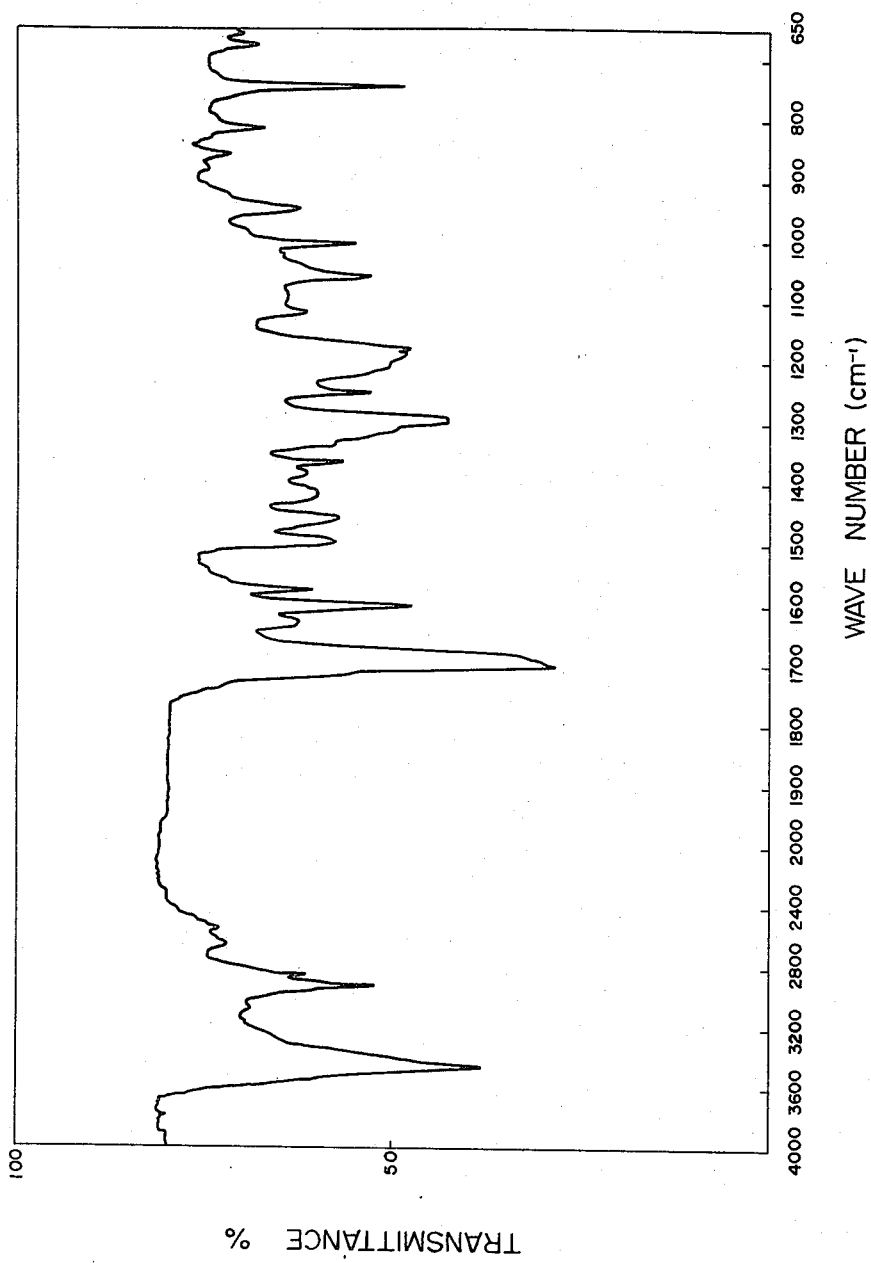
FIGS. 1 and 2 are the IR and NMR spectrum of the novel compound, N-methyl-N-(2-hydroxy-3-methacryloyloxypropyl)-m-aminobenzoic acid, respectively.
Figure 2:
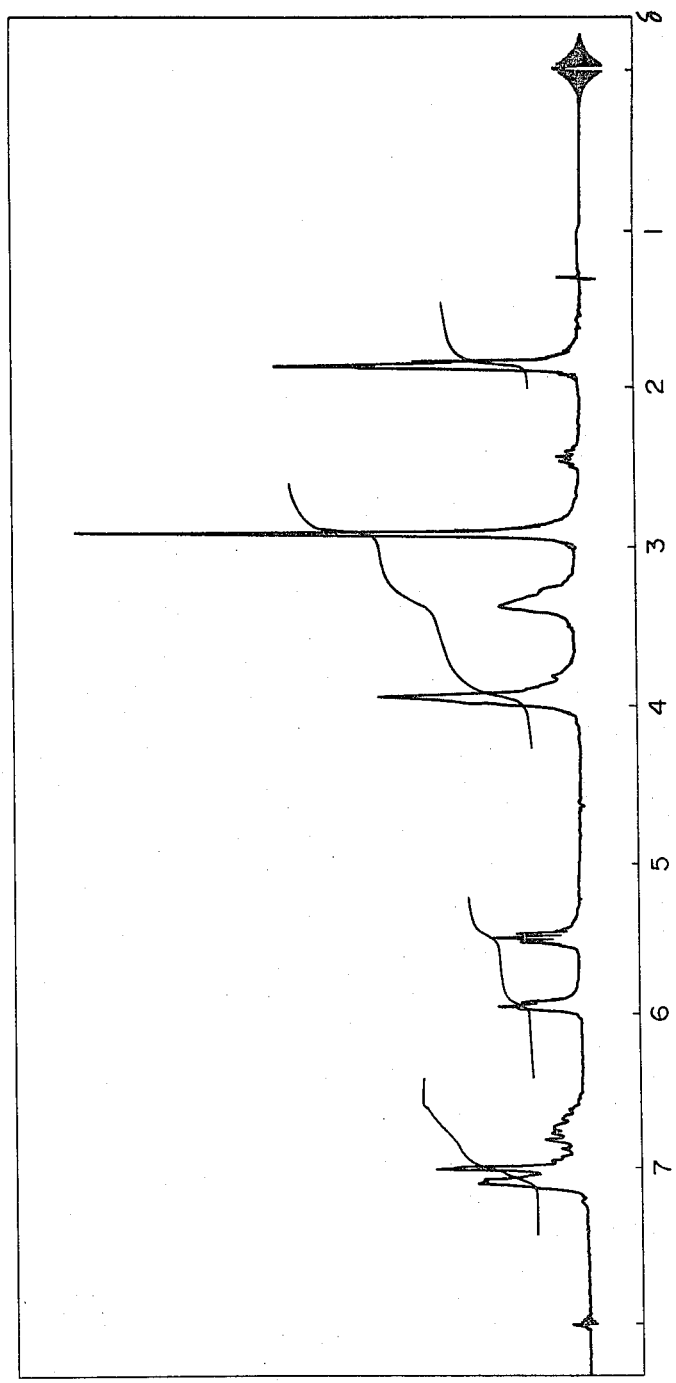

The novel compound of formula (2), that is, N-methyl-N-(2-hydroxy-3-methacryloyloxypropyl)-m-aminobenzoic acid is obtained in the form of pale yellow crystalline powder which has a melting point of 134.0°–135.0° C., and the infrared absorption spectrum as shown in FIG. 1 and the NMR spectrum as shown in FIG. 2. This novel compound of formula (2) may be prepared by reacting glycidyl methacrylate with m-(methylamino)-benzoic acid in a suitable solvent such as methanol under reflux.

Figure 3:
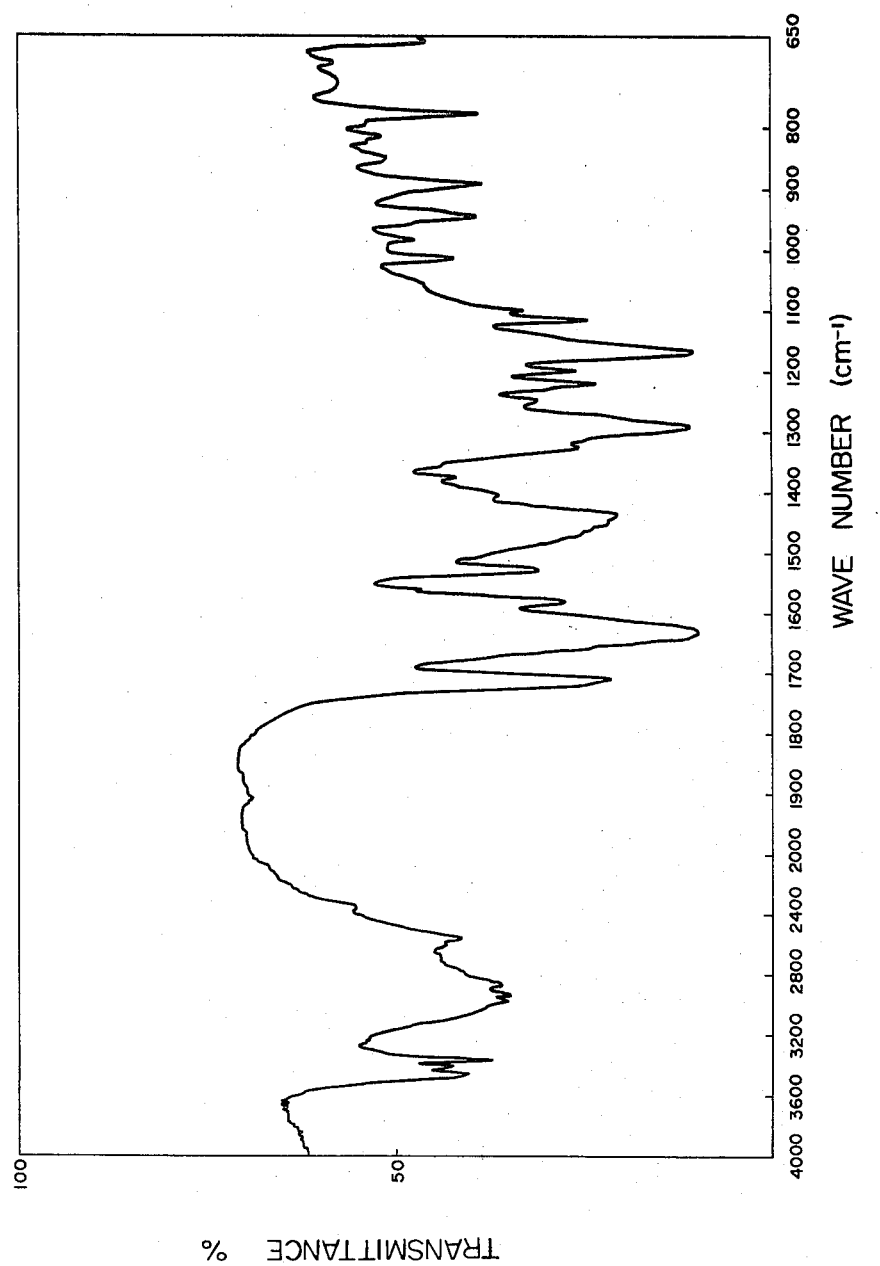
FIGS. 3 and 4 are the IR and NMR spectrum of the novel compound, 2-hydroxy-4-[(2-hydroxy-3-methacryloyloxypropyl)amino]benzoic acid, respectively.
Figure 4:
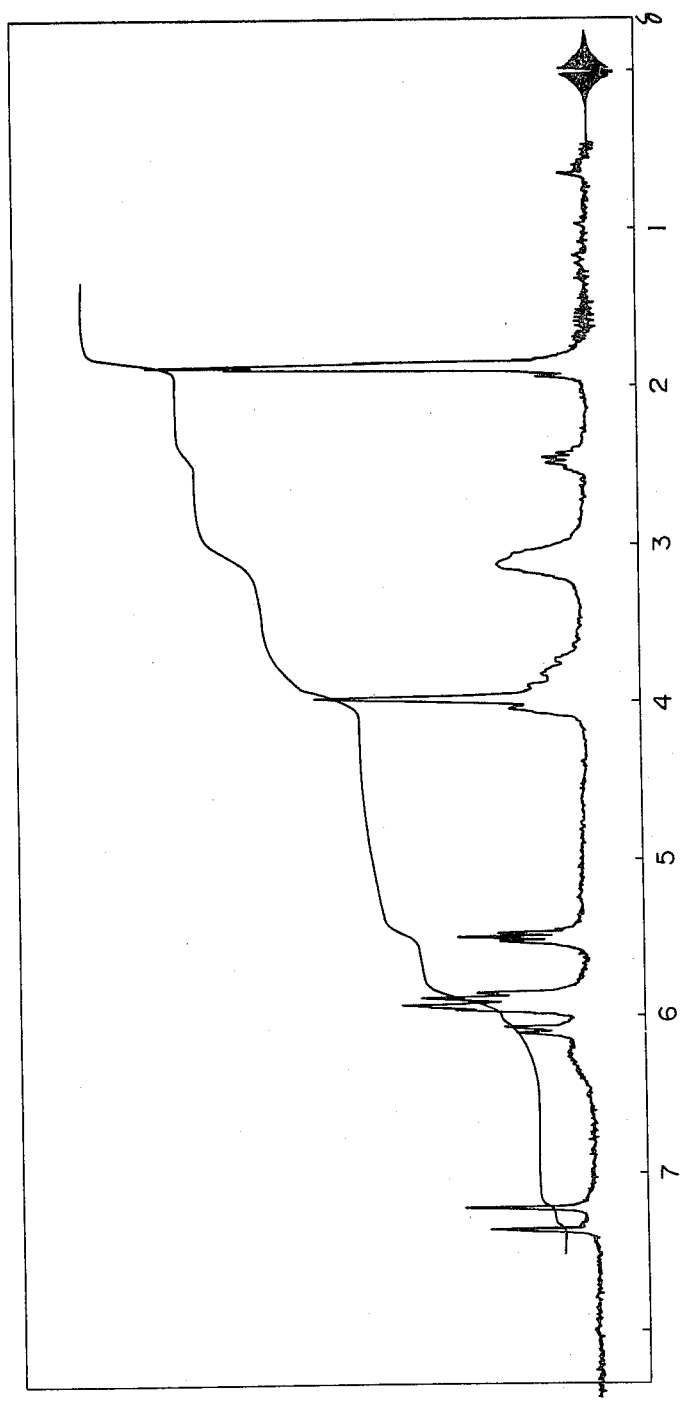

The novel compound of formula (3), that is, 2-hydroxy-4-[(2-hydroxy-3-methacryloyloxypropyl)amino]-benzoic acid is obtained in the form of white crystal which has a melting point of 140.5°–143.5° C., and the infrared absorption spectrum as shown in FIG. 3 and the NMR spectrum as shown in FIG. 4. This novel compound of formula (3) may be prepared by reacting glycidyl methacrylate with p-aminosalicylic acid, for example, in an aqueous caustic alkali solution.

The compounds of the present invention may be used as polymerizable monomers in a dental adhesive composition of the type where the polymerizable monomer is polymerized upon use. The compounds of formula (1) may be used either alone as sole polymerizable monomers or in admixture with any desired other polymerizable monomers. The compounds of formula (1) may be polymerized or cured into homopolymers or copolymers with other monomers, which can firmly adhere to tooth.

Dental adhesive compositions containing one or both of the compounds of formula (1) may be used for the purpose of adhesion to tooth. The composition may be used as a filling material or an orthodontic adhesive. The composition may also be used as a primer or undercoat for assisting in adhering a filling material such as a composite resin or an orthodontic adhesive to a tooth.

When the compounds of formula (1) are used as polymerizable monomers in a dental adhesive composition, the composition may contain any additional ingredients generally used for such a purpose although the actual choice of ingredients depends on the type and intended use of a particular composition.

When a dental adhesive composition is used as an adhesive filling material, the compounds of formula (1) may be sole polymerizable monomers which may be polymerized or cured in the presence of a curing agent into a cured material applicable as an adhesive filling material. Preferably, the dental adhesive composition used as the adhesive filling material comprises a mixture of one or both of the compounds of formula (1) and other polymerizable monomers, which may be polymerized or cured in the presence of a curing agent upon use.

The other monomers which can be used in combination with the compounds of formula (1) may be mono- or polyfunctional groups. Examples of the monofunctional and polyfunctional monomers are enumerated below.

Monofunctional Monomer methyl acrylate and methacrylate,
ethyl acrylate and methacrylate,
butyl acrylate and methacrylate,
allyl acrylate and methacrylate,
hydroxyethyl acrylate and methacrylate,
methoxyethyl acrylate and methacrylate,
glycidyl acrylate and methacrylate,
tetrahydrofurfuryl acrylate and methacrylate,
styrene, etc.

Polyfunctional Monomer

Difunctional aliphatic acrylate and methacrylate ethylene glycol diacrylate and dimethylacrylate,
diethylene glycol diacrylate and dimethacrylate,
triethylene glycol diacrylate and dimethacrylate,
tetraethylene glycol diacrylate and dimethacrylate,
polyethylene glycol diacrylate and dimethacrylate,
butylene glycol diacrylate and dimethacrylate,
neopentyl glycol diacrylate and dimethacrylate,
propylene glycol diacrylate and dimethacrylate,
1,3-butanediol diacrylate and dimethacrylate,
1,4-butanediol diacrylate and dimethacrylate,
1,6-hexanediol diacrylate and dimethacrylate, etc.

Difunctional aromatic acrylate and methacrylate 2,2-bis(acryloxyphenyl)propane,
2,2-bis(methacryloxyphenyl)propane,
2,2-bis(4-(3-acryloxy)-2-hydroxypropoxyphenyl)propane,
2,2-bis(4-(3-methacryloxy)-2-hydroxypropoxyphenyl)propane,
2,2-bis(4-acryloxyethoxyphenyl)propane,
2,2-bis(4-methacryloxyethoxyphenyl)propane,
2,2-bis(4-acryloxydiethoxyphenyl)propane,
2,2-bis(4-methacryloxydiethoxyphenyl)propane,
2,2-bis(4-acryloxytriethoxyphenyl)propane,
2,2-bis(4-methacryloxytriethoxyphenyl)propane,
2,2-bis(4-acryloxytetraethoxyphenyl)propane,
2,2-bis(4-methacryloxytetraethoxyphenyl)propane,
2,2-bis(4-acryloxypentaethoxyphenyl)propane,
2,2-bis(4-methacryloxypentaethoxyphenyl)propane,
2,2-bis(4-acryloxybutoxyphenyl)propane,
2,2-bis(4-methacryloxybutoxyphenyl)propane,
2,2-bis(4-acryloxydibutoxyphenyl)propane,
2,2-bis(4-methacryloxydibutoxyphenyl)propane,
2,2-bis(4-acryloxydipropoxyphenyl)propane,
2,2-bis(4-methacryloxydipropoxyphenyl)propane,
2,2-bis(4-acryloxytripropoxyphenyl)propane,
2,2-bis(4-methacryloxytripropoxyphenyl)propane,
2-(4-acryloxyethoxyphenyl)-2-(4-acryloxydiethoxyphenyl)propane,
2-(4-methacryloxyethoxyphenyl)-2-(4-methacryloxydiethoxyphenyl)propane,
2-(4-acryloxydiethoxyphenyl)-2-(4-acryloxytriethoxyphenyl)propane,
2-(4-methacryloxydiethoxyphenyl)-2-(4-methacryloxytriethoxyphenyl)propane,
2-(4-acryloxydipropoxyphenyl)-2-(4-acryloxytriethoxyphenyl)propane,
2-(4-methacryloxydipropoxyphenyl)-2-(4-methacryloxytriethoxyphenyl)propane,
2,2-bis(4-acryloxypropoxyphenyl)propane,
2,2-bis(4-methacryloxypropoxyphenyl)propane,
2,2-bis(4-acryloxyisopropoxyphenyl)propane,
2,2-bis(4-methacryloxyisopropoxyphenyl)propane, xylylene glycol diacrylate,
xylylene glycol dimethacrylate,
bis(ethyleneoxide)bisphenol-A diacrylate and methacrylate, etc.

Trifunctional aliphatic acrylate and methacrylate trimethylolpropane triacrylate and trimethacrylate,
trimethylolethane triacrylate and trimethacrylate,
trimethylolethanol triacrylate and trimethacrylate,
trimethylolmethane triacrylate and trimethacrylate,
pentaerythritol triacrylate and trimethacrylate, etc.

Tetrafunctional acrylate and methacrylate tetramethylolmethane tetraacrylate and tetramethacrylate, etc.

In the adhesive filling material, oligomers and polymers may be blended in an amount of 0–30% by weight of the polymerizable monomers with the above-mentioned monomers for the purpose of regulating viscosity, curing rate and curing shrinkage. The oligomers and polymers include those of the compounds of formula (1), methyl acrylate, methyl methacrylate, hydroxyethyl acrylate, hydroxyethyl methacrylate, tetrahydrofurfuryl acrylate, tetrahydrofurfuryl methacrylate, glycidyl acrylate, glycidyl methacrylate, styrene, and the like.

Also included are fillers which serve to increase the compressive strength, hardness and other physical properties of a cured product. Inorganic fillers are usually employed although organic fillers may be employed to improve surface gloss of a cured product and the affinity or bonding with polymerizable monomers. The inorganic fillers include alpha-quartz, fumed silica, glass beads, aluminum oxide, and the like. The particle size is not particularly limited although fillers having a particle size of less than 100 microns, especially less than 50 microns are preferred. Those fillers having a particle size as small as several microns or less are also preferred to increase surface smoothness. Also included is a combination of particles having a size of several ten microns and particles having a size of several microns. The inorganic fillers may preferably be pretreated with a silane coupling agent in order to obtain an improved bonding with monomers. Examples of the silane coupling agent for such pretreatment are vinyl trichlorosilane, vinyl triethoxysilane, vinyl trimethoxysilane, vinyl tris($\beta$-methoxyethoxy)silane, $\gamma$-methacryloxypropyl trimethoxysilane, N-($\beta$-aminoethyl)-$\gamma$-aminopropyl trimethoxysilane, and the like. The organic fillers which can be employed herein are those prepared by finely dividing a polymer of any of the above-mentioned monomers to a particle size of less than 50 microns in a ball mill or any suitable means. Another procedure to prepare organic fillers is polymerization of monomers dispersing inorganic fillers having a particle size of less than 10 microns. The polymerization cured product is finely divided to a particle size of less than 50 microns in a ball mill or any suitable means. It is to be noted that the filler may be blended in an amount of 50–85% by weight of the total weight of a filling material.

Polymerization inhibitors, coloring agents, antioxidants and other well-known ingredients may be blended.

Catalysts or curing agents may also be blended in the filling material. Any suitable known catalysts or curing agents may be used, for example, a combination of an amine and a peroxide, or sulfinic acid or its derivatives and a peroxide. When the compounds of formula (1) are sole polymerizable monomers, the monomer may be divided into two equal parts. One part contains a first curing agent, for example, an amine or p-toluene sulfinic acid and the other part contains a second curing agent, for example, a peroxide. When the compounds of formula (1) are to be mixed with other polymerizable monomers, the other monomers may be divided into two equal parts. One part contains a first curing agent and the other part contains a second curing agent. The compounds of formula (1) may be added to either or both of the two parts, which are to be mixed upon use. In both cases, other additional ingredients may be added to either or both of the two parts. Immediately before application, these two parts are blended into a mixture which will cure by nature. The amine may include N,N-dimethyl-p-toluidine, N,N'-di($\beta$-hydroxyethyl)-p-toluidine, N,N-dimethyl aniline, monoethanol amine and the like. The content of the amine may preferably be in the range of from 0.1 to 5% by weight of the polymerizable monomers. Derivatives of sulfinic acid may be benzene sulfinic acid, p-toluene sulfinic acid and their sodium salts, and the like. The content of sulfinic acid or its derivatives may preferably be in the range of from 2 to 6% by weight of the polymerizable monomers. The peroxide may include benzoyl peroxide, di-p-chloro-benzoyl peroxide, di-lauroyl-peroxide, methyl ethyl ketone peroxide and the like. The content of the peroxide may preferably be in the range of from 0.1 to 3% by weight of the polymerizable monomers.

The filling material may also be formulated into an ultraviolet curable system by blending an ultraviolet sensitizer such as benzoin methyl ether, acetophenone, benzophenone, 2,2,2-trichloro-4'-t-buthylacetophenone, anthraquinone and the like in an amount of 0.3–3% by weight of the monomers. In this case, all the necessary ingredients may be blended into a single composition which must be packed in a UV-shielded package.

The compounds of formula (1) may be blended in varying, unlimited amounts in the adhesive filling material. When the compounds of formula (1) are used in combination with other polymerizable monomers as described above, the compounds may preferably be 1–30% by weight, particularly 2–15% by weight based on the other polymerizable monomers. Poor adhesion results from amounts of less than 1% whereas cured products have sometimes reduced hardness with amounts of more than 30%. It is to be noted that the adhesive filling material may preferably comprise 10–45% by weight of a polymerizable monomer or monomers and 50%–85% by weight of an inorganic filler.

When a dental adhesive composition containing one or both of the compounds of formula (1) is used as an adhesive for adhering a conventional filling material such as a composite resin to tooth, this composition may be prepared by adding 1–15% by weight of one or both of the compounds of formula (1) to a suitable organic solvent such as ethanol, diethyl ether and chloroform preferably at a concentration of 0.5–30% by weight. Another preferred composition may be prepared by mixing 1–15% by weight of the composition of one or both of the compounds of formula (1) with other polymerizable monomers. The mixture may be dissolved into a suitable solvent. A further preferred composition may be prepared by using the same formulation as described for the adhesive filling material. It should be noted that improved adhesion cannot be achieved when the compounds of formula (1) are present in extremely smaller or larger proportions.

These dental adhesive compositions may be applied or cured in a manner depending on their type and intended use. When the composition is used as a filling material, this adhesive composition or filling material may be introduced into a cavity to be filled and then cured in situ. When the composition is used for the purpose of adhesion of a dental filling material to tooth, this adhesive composition may be applied to the wall of a cavity to be filled before the cavity is filled with a desired filling material which is then cured in situ.

Dental adhesive compositions containing the compounds of formula (1) according to the present invention can maintain a high degree of adhesion even in water or saliva because polymers of the compounds of formula (1) have improved adhesion to tooth substances. The compositions are highly durable in mouth. When the composition is used as a filling material, it firmly adheres to tooth for a long period of time even in wet, temperature-varying environment as in mouth. When the composition is used for the purpose of adhesion as a primer or undercoat for a composite resin or orthodontic adhesive, it firmly adheres to tooth as well as to the composite resin or orthodontic adhesive and prevents a gap from forming between tooth and the composite resin or orthodontic adhesive, thereby providing sufficient marginal sealing to control secondary caries.

The examples of the present invention are set forth below by way of illustration and not by way of limitation.

EXAMPLE 1

Preparation of N-methyl-N-(2-hydroxy-3-methacryloyloxypropyl)-m-aminobenzoic acid A 30-ml flask equipped with a reflux condenser was charged with 1.42 g (0.01 mol) of glycidyl methacrylate, 1.51 g (0.01 mol) of m-(methylamino)benzoic acid and 10 ml of methyl alcohol, and the contents were refluxed for 2.5 hours with stirring. Thereafter, the methyl alcohol was distilled off in vacuum and the reaction solution was then allowed to stand until crude yellow crystals precipitated. Recrystallization from chloroform gave 2.1 g (yield 72%) of a pure pale yellow crystalline powder, which was identified to be N-methyl-N-(2-hydroxy-3-methacryloyloxypropyl)-m-aminobenzoic acid.

Melting point: 134.0°–135.0° C.

Elemental analysis for $C_{15}H_{19}O_5N$: Calculated: C 61.42%, H 6.53%, N 4.78%; Found: C 61.46%, H 6.52%, N 4.72%.

Infrared absorption spectrum (KBr): FIG. 1. Absorption peaks at 3450 cm$^{-1}$ (hydrogen attributable to ring opening of epoxy ring), 1700 and 1680 cm$^{-1}$ (carbonyl), 1600 and 1580 cm$^{-1}$ (benzene ring), and 1300 and 1180 cm$^{-1}$ (ester).

NMR spectrum (DMSO-d$_6$): FIG. 2. $\delta$5.50 and 5.90 (integration strength ratio 1) indicating the presence of $CH_2=$, $\delta$1.88 (integration strength ratio 3) indicating the presence of $-CH_3$, $\delta$2.92 (integration strength ratio 3) indicating the presence of $-N-CH_3$, and $\delta$6.60–7.22 (integration strength ratio 4) indicating the presence of hydrogens of benzene ring.

EXAMPLE 2

Preparation of 2-hydroxy-4-[(2-hydroxy-3-methacryloyloxypropyl)amino]benzoic acid A 30-ml flask was charged 1.13 g (0.02 mol) of potassium hydroxide in 10 ml of water. To the solution were added 3.06 g (0.02 mol) of p-aminosalicylic acid and 3.43 g (0.024 mol) of glycidyl methacrylate. The mixture was stirred at room temperature for 5 hours. After cooled to 0° C., the reaction solution was adjusted to pH 4 by adding dropwise 2 N hydrochloric acid in water, and then extracted with diethyl ether. The ether phase was dried with anhydrous magnesium sulfate and the ether was distilled off in vacuum, leaving crude white crystals. Recrystallization from an ethyl acetate/petroleum ether mixed solvent gave 2.8 g (yield 47.5%) of pure white crystals which were identified to be 2-hydroxy-4-[(2-hydroxy-3-methacryloyloxypropyl)amino]benzoic acid.

Melting point: 140.5°–143.5° C.

Elemental analysis for $C_{14}H_{17}O_6N$: Calculated: C 56.94%, H 5.80%, N 4.74%; Found: C 56.83%, H 5.79%, N 4.65%.

Infrared absorption spectrum (KBr): FIG. 3. Absorption peaks at 1715 cm$^{-1}$ (carbonyl), 1640 and 1590 cm$^{-1}$ (benzene ring), 1300 and 1160 cm$^{-1}$ (ester).

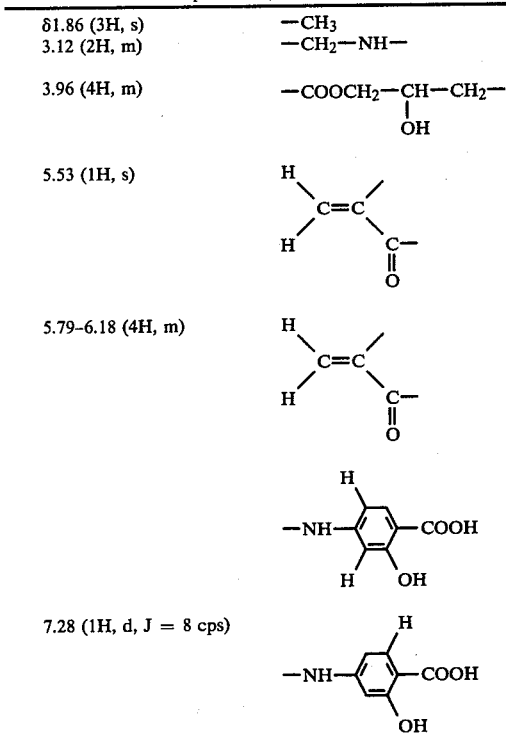

NMR spectrum (DMSO—d$_6$): FIG. 4

In the following examples, application of the compounds of the present invention to tooth substances is illustrated. All parts and percentages are by weight.

EXAMPLE 3

Primers or dental adhesive compositions were prepared by dissolving the compounds of formulas (2) and (3) in ethanol at a concentration of 5%.

A bovine tooth embedded in a holder with a gypsum binder and an acrylic rod (6 mm diameter, 40 mm long) were finished so as to have a given degree of surface smoothness by means of a polisher. The finished surface of the bovine tooth was treated with 3 M phosphoric acid for 30 seconds, rinsed with water for 30 minutes, and then dried with compressed-air blast. The above-prepared primer was applied to the dried tooth surface and dried before the acrylic rod was attached thereto using an adhesive polymer of the following formulation. The assembly was stored in artificial saliva at a temperature of 37° C. After storage for 14 and 60 days, adhesion was measured using a Strograph at a pulling rate of 5 mm/min. The results are shown in Table 1.

| Formulation of the adhesive polymer | | |
|---|---|---|
| | | Parts by weight |
| (a) | Methyl methacrylate | 2 |
| | Polymethyl methacrylate | 0.4 |
| | N,N—dimethyl-p-toluidine | 0.04 |
| (b) | Methyl methacrylate | 2 |
| | Polymethyl methacrylate | 0.4 |
| | Benzoyl peroxide | 0.04 |

Portions (a) and (b) were mixed at a weight ratio of 1:1 immediately before application.

TABLE 1

| | Bond strength, kg/cm$^2$ | |
|---|---|---|
| | 14 days | 60 days |
| Compound (2) | 147 | 152 |
| Compound (3) | 159 | 174 |

As seen from Table 1, the compounds of formulas (2) and (3) according to the present invention provide increased bond strengths.

EXAMPLE 4

A mixture was prepared by thoroughly mixing 10 parts of methyl methacrylate, 20 parts of diethylene glycol dimethacrylate, 50 parts of bisphenol-A diglycidyl methacrylate and 350 parts of silane-coupled quartz sand having a particle size of less than 50 microns, and divided into two equal portions. Then 6 parts of the compound of the present invention and 2 parts of N,N-dimethyl-p-toluidine were added to one portion, while 2 parts of benzoyl peroxide was added to the other portion. These two portions were mixed together. Using the resulting mixture, an acrylic rod was attached to a bovine tooth at their smoothly finished surfaces in the same manner as in Example 3. Using the Strograph, the adhesion was measured to be 85 and 98 kg/cm$^2$ (average) for the compounds of formulas (2) and (3), respectively, after one week storage in water.

EXAMPLE 5

A cavity having a diameter of 4 mm and a depth of 2-2.5 mm was prepared in an extracted human tooth at the labial surface. The cavity wall was etched with 3 M phosphoric acid for 30 seconds. A solution consisting of 10 parts of the compound of the present invention, 60 parts of methyl methacrylate and 30 parts of tetraethylene glycol dimethacrylate was then applied to the etched wall of the cavity, which was filled with Adaptic (trade mark, manufactured by Johnson & Johnson Co.). After the thus filled tooth was allowed to stand for 30 minutes for curing, it was immersed in water at a temperature of 37° C. for one day. Thereafter, the tooth was subjected to a percolation test in which the tooth sample was alternately dipped in aqueous Fuchsine solutions at 4° C. and 60° C. each for one minute and 60 times for each solution. This percolation test was designed to examine marginal sealing. The tooth was cut at the center into two to examine at the cross section whether or not the dyestuff (Fuchsine) had penetrated between the cavity wall and the filling material. No penetration of the dyestuff was observed for both the compounds of formulas (2) and (3).

When a tooth cavity was filled with Adaptic without pre-treatment with the solution containing the compound of the present invention, it was found that the dyestuff (Fuchsine) had penetrated along the cavity wall to the dentinal portion or to the cavity floor. These results prove that the compounds of the present invention are also effective for adhesion between the tooth and a filling material.

What is claimed is:

1. An N-(2-hydroxy-3-methacryloyloxypropyl)-aminobenzoic acid derivative having the general formula:

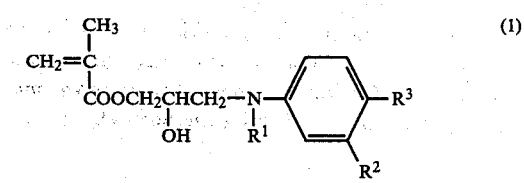

wherein R$^2$ is a carboxyl group and R$^3$ is a hydrogen atom when R$^1$ is a methyl group, and R$^2$ is a hydroxyl group and R$^3$ is a carboxyl group when R$^1$ is a hydrogen atom.

2. The compound according to claim 1 which is N-methyl-N-(2-hydroxy-3-methacryloyloxypropyl)-m-aminobenzoic acid having the formula:

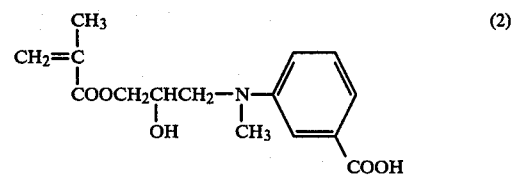

3. The compound according to claim 1 which is 2-hydroxy-4-[(2-hydroxy-3-methacryloyloxypropyl)amino]-benzoic acid having the formula:

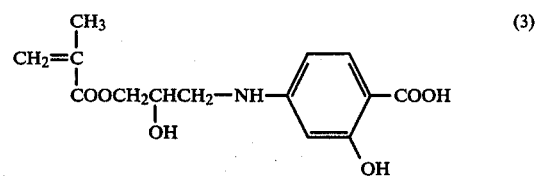

4. A dental adhesive composition comprising an N-(2-hydroxy-3-methacryloyloxypropyl)aminobenzoic acid derivative having the general formula:

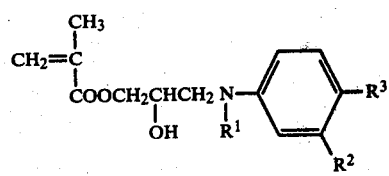

wherein $R^2$ is a carboxyl group and $R^3$ is a hydrogen atom when $R^1$ is a methyl group, and $R^2$ is a hydroxyl group and $R^3$ is a carboxyl group when $R^1$ is a hydrogen atom.

5. A dental adhesive composition according to claim 4 wherein the aminobenzoic acid derivative is N-methyl-N-(2-hydroxy-3-methacryloyloxypropyl)-m-aminobenzoic acid having the formula:

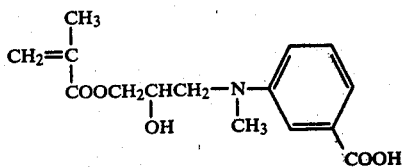

6. A dental adhesive composition according to claim 4 wherein the aminobenzoic acid derivative is 2-hydroxy-4-[(2-hydroxy-3-methacryloyloxypropyl)amino]benzoic acid having the formula:

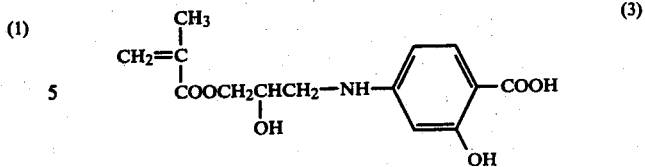

7. A dental adhesive composition according to claim 4, wherein said N-(2-hydroxy-3-methacryloyloxypropyl)aminobenzoic acid derivative having the formula (1) is present in the composition in combination with other polymerizable monomers in an amount of 1-30% by weight based on the other polymerizable monomers.

8. A dental adhesive composition according to claim 4, wherein said N-(2-hydroxy-3-methacryloyloxypropyl)aminobenzoic acid derivative having the formula (1) is present in the composition in combination with other polymerizable monomers in an amount of 2-15% by weight based on the other polymerizable monomers.

9. A dental adhesive composition according to claim 4, wherein said composition comprises 50-85% by weight of an inorganic filler.

10. A dental adhesive composition according to claim 4, wherein said N-(2-hydroxy-3-methacryloyloxypropyl)aminobenzoic acid having the formula (1) is present in the composition in combination with at least one other polymerizable monomer.

* * * * *